(12) United States Patent
Hu et al.

(10) Patent No.: US 12,153,175 B2
(45) Date of Patent: Nov. 26, 2024

(54) METHOD AND TERMINAL DEVICE FOR PROCESSING POSITRON EMISSION TOMOGRAPHY DATA

(71) Applicant: SHENZHEN INSTITUTES OF ADVANCED TECHNOLOGY CHINESE ACADEMY OF SCIENCES, Guangdong (CN)

(72) Inventors: Zhanli Hu, Guangdong (CN); Yongfeng Yang, Guangdong (CN); Chunhui Zhang, Guangdong (CN); Zhonghua Kuang, Guangdong (CN); Xiaohui Wang, Guangdong (CN); San Wu, Guangdong (CN); Dong Liang, Guangdong (CN); Xin Liu, Guangdong (CN); Hairong Zheng, Guangdong (CN)

(73) Assignee: SHENZHEN INSTITUTES OF ADVANCED TECHNOLOGY CHINESE ACADEMY OF SCIENCES, Guangdong (CN)

( * ) Notice: Subject to any disclaimer, the term of this patent is extended or adjusted under 35 U.S.C. 154(b) by 360 days.

(21) Appl. No.: 17/824,453

(22) Filed: May 25, 2022

(65) Prior Publication Data

US 2022/0283325 A1  Sep. 8, 2022

Related U.S. Application Data

(63) Continuation-in-part of application No. PCT/CN2019/120514, filed on Nov. 25, 2019.

(51) Int. Cl.
*G01T 1/29* (2006.01)
*A61B 6/00* (2024.01)
(Continued)

(52) U.S. Cl.
CPC ............ *G01T 1/2985* (2013.01); *A61B 6/037* (2013.01); *A61B 6/5205* (2013.01); *G06T 11/003* (2013.01)

(58) Field of Classification Search
CPC ..... G01T 1/2985; A61B 6/037; A61B 6/4258; A61B 6/5205; G06T 11/00; G06T 11/003
(Continued)

(56) References Cited

U.S. PATENT DOCUMENTS 9,990,718 B2 * 6/2018 Feng ............... G06T 11/003
2007/0278410 A1 * 12/2007 Cho ................ G06T 11/006
250/363.03
(Continued)

FOREIGN PATENT DOCUMENTS

CN          104183012 A      12/2014
CN          106539591 A  *   3/2017  ......... G01N 23/2206
(Continued)

*Primary Examiner* — Mahendra R Patel
(74) *Attorney, Agent, or Firm* — Brooks Kushman P.C.

(57) ABSTRACT

A method for processing positron emission tomography data is provided, this method includes: obtaining a first coordinate and a second coordinate respectively corresponding to two ends of a response line to be processed; determining corresponding dimensional coordinates of the response line to be processed in a sinogram based on the first coordinate and the second coordinate; and generating the sinogram corresponding to the response line to be processed based on the dimensional coordinates. According to this method, the amount of calculation of system matrix is reduced, the accuracy of position information of the generated response line is improved, and the accuracy of generated sinogram is improved accordingly.

18 Claims, 3 Drawing Sheets

Obtain a first coordinate and a second coordinate respectively corresponding to two ends of a response line to be processed from a positron emission tomography device ⟶ S101

Determine corresponding dimensional coordinates of the response line to be processed in a sinogram corresponding to the response line to be processed based on the first coordinate and the second coordinate ⟶ S102

Generate the sinogram corresponding to the response line to be processed based on the dimensional coordinates of the response line to be processed ⟶ S103

(51) Int. Cl.
*A61B 6/03* (2006.01)
*G06T 11/00* (2006.01)

(58) Field of Classification Search
USPC .......................................................... 382/131
See application file for complete search history.

(56) References Cited

U.S. PATENT DOCUMENTS

| | | | | |
|---|---|---|---|---|
| 2009/0262996 | A1* | 10/2009 | Samsonov | G01R 33/5611 |
| | | | | 382/130 |
| 2010/0098312 | A1* | 4/2010 | Leahy | G06T 11/005 |
| | | | | 382/131 |
| 2016/0163095 | A1* | 6/2016 | Wollenweber | A61B 6/037 |
| | | | | 382/131 |
| 2017/0084025 | A1* | 3/2017 | Lyu | G06T 7/70 |
| 2019/0251713 | A1* | 8/2019 | Chen | A61B 6/482 |
| 2019/0374105 | A1* | 12/2019 | Raylman | A61B 6/4417 |
| 2020/0029928 | A1* | 1/2020 | Wollenweber | A61B 5/0037 |

FOREIGN PATENT DOCUMENTS

| | | | | |
|---|---|---|---|---|
| CN | 106821402 A | * | 6/2017 | |
| CN | 109498048 A | | 3/2019 | |
| JP | 4208284 B2 | * | 1/2009 | ............. G01T 1/172 |
| WO | WO-9530159 A1 | * | 11/1995 | ............. A61B 6/037 |
| WO | WO-2005078632 A2 | * | 8/2005 | ............. A61B 6/027 |
| WO | WO-2008067842 A1 | * | 6/2008 | ........... G06T 11/006 |
| WO | WO-2008075037 A1 | * | 6/2008 | ........... G01T 1/1647 |
| WO | WO-2008146186 A2 | * | 12/2008 | ............. A61B 6/037 |
| WO | WO-2008156764 A1 | * | 12/2008 | ............. A61B 6/5264 |
| WO | WO-2009082736 A1 | * | 7/2009 | ............. A61B 6/037 |
| WO | WO-2013177661 A1 | * | 12/2013 | ............. A61B 6/037 |
| WO | WO-2021072416 A1 | * | 4/2021 | ............. A61B 6/037 |
| WO | WO-2021102614 A1 | * | 6/2021 | ........... G06T 11/003 |
| WO | WO-2021145856 A1 | * | 7/2021 | ............. A61B 6/037 |

* cited by examiner

METHOD AND TERMINAL DEVICE FOR PROCESSING POSITRON EMISSION TOMOGRAPHY DATA

CROSS-REFERENCE TO RELATED APPLICATION

This application is a continuation-in-part of PCT patent application Ser. No. PCT/CN2019/120514, filed on Nov. 25, 2019, the entire contents of which are incorporated herein by reference.

TECHNICAL FIELD

The present application relates to the technical field of computers, and more particularly to a method for processing positron emission tomography data, and a terminal device for processing positron emission tomography data.

DESCRIPTION OF RELATED ART

Currently, with the development of society, PET (Positron Emission Tomography) devices have been widely used in the medical field. PET is a medical imaging technology that uses a positron nuclide as a tracer, uptakes the positron nuclide through a part of a human body and reflects a metabolic change in the human body, and obtains an internal image of the human body through scanning using a positron scanning machine. That is, a PET image may be generated by the PET device, and a disease analysis may be performed according to the PET image.

A very important step in generation of the PET image is to convert a response line detected by a detector of the PET device into a sinogram. However, the traditional method for converting sinogram increases the calculation amount of system matrix, and the position information of the response line is inaccurate, so that a generated sinogram is inaccurate, a low quality and a poor definition of the PET image generated according to the sinogram are further caused.

SUMMARY

One of the objectives of the embodiments of the present application is to provide a method and a terminal device for processing PET data, which aims to solve a technical problem that the use of the traditional PET data conversion method increases the calculation amount of the corresponding system matrix, so that the determined position information of the response line is inaccurate, the sinogram generated according to the response line is inaccurate, and thus a poor quality and low definition of the generated PET image are further caused.

In order to solve the technical problem mentioned above, the technical solutions used in the embodiments of the present application are as follows:

in the first aspect, a method for processing positron emission tomography data is provided, this method is implemented by a terminal device and includes:
  obtaining a first coordinate and a second coordinate respectively corresponding to two ends of a response line to be processed from a positron emission tomography device, where the response line to be processed refers to a response line obtained by detecting electrons using a detector in the positron emission tomography device;
  determining corresponding dimensional coordinates of the response line to be processed in a sinogram corresponding to the response line to be processed based on the first coordinate and the second coordinate; and
  generating the sinogram corresponding to the response line to be processed based on the dimensional coordinates and generating a positron emission tomography image based on the sinogram which is generated based on the dimensional coordinates.

In one embodiment, in order to accurately obtain the coordinates respectively corresponding to the two ends of the response line to be processed, said obtaining the first coordinate and the second coordinate respectively corresponding to the two ends of the response line to be processed from the positron emission tomography device includes:
  obtaining and storing crystal coordinates and crystal numbers of a plurality of crystals from the positron emission tomography device;
  obtaining a first crystal number and a second crystal number respectively corresponding to the two ends of the response line to be processed sent from the positron emission tomography device; and
  determining the first coordinate corresponding to the first crystal number and determining the second coordinate corresponding to the second crystal number based on the crystal coordinates and the crystal numbers of the crystals, and the first crystal number and the second crystal number respectively corresponding to the two ends of the response line to be processed.

In one embodiment, in order to accurately calculate the coordinates of the response line to be processed in the sinogram, said determining the dimensional coordinates of the response line to be processed in the sinogram corresponding to the response line to be processed includes:
  adding a preset random number to the first coordinate and the second coordinate respectively to obtain a first continuous coordinate corresponding to the first coordinate and a second continuous coordinate corresponding to the second coordinate; and
  obtaining the dimensional coordinates based on the first continuous coordinate and the second continuous coordinate.

In one embodiment, in order to accurately calculate the dimensional coordinates to enable the determined dimensional coordinates to reflect the physical position of the response line to be processed more accurately, said obtaining the dimensional coordinates based on the first continuous coordinate and the second continuous coordinate includes:
  determining a target response line corresponding to the response line to be processed based on the first continuous coordinate and the second continuous coordinate;
  projecting the target response line on a preset plane to obtain a projected response line;
  determining a first dimensional coordinate and a second dimensional coordinate corresponding to the target response line based on the first continuous coordinate, the second continuous coordinate and the projected response line;
  determining a third dimensional coordinate and a fourth dimensional coordinate corresponding to the target response line; and
  generating the dimensional coordinates based on the first dimensional coordinate, the second dimensional coordinate, the third dimensional coordinate, and the fourth dimensional coordinate.

In one embodiment, in order to accurately calculate the dimensional coordinates to enable the determined dimensional coordinates to reflect the physical position of the response line to be processed more accurately, said determining the first dimensional coordinate and the second dimensional coordinate corresponding to the target response line based on the first continuous coordinate, the second continuous coordinate and the projected response line includes:
  determining a vertical distance from the projected response line to a preset original point based on the first continuous coordinate and the second continuous coordinate;
  determining an included angle formed between the projected response line and a preset horizontal direction based on the first continuous coordinate and the second continuous coordinate; and
  obtaining the first dimensional coordinate and the second dimensional coordinate based on the vertical distance from the projected response line to the preset original point, and the included angle.

In one embodiment, in order to represent the physical position of the response line to be processed more accurately, thereby making the generated sinogram to be more accurate, performing a weighting processing on the response line generated based on the dimensional coordinates in the sinogram.

In one embodiment, in order to perform the weighting processing accurately, said performing the weighting processing on the response line generated based on the dimensional coordinates in the sinogram includes:
  determining a weighted value based on the first dimensional coordinate, the second dimensional coordinate, the third dimensional coordinate, and the fourth dimensional coordinate; and
  performing, based on the weighted value, the weighting processing on the response line generated based on the dimensional coordinates.

In the second aspect, a terminal device for processing positron emission tomography data is provided, this terminal includes a processor, an input device, an output device and a memory, the processor, the input device, the output device and the memory are mutually connected, where the memory is used to store a computer program that supports the processor on executing the aforesaid method, the computer program includes a computer program instruction, when executing the computer program, the processor is configured to:
  obtain a first coordinate and a second coordinate respectively corresponding to two ends of a response line to be processed from a positron emission tomography device, where the response line to be processed refers to a response line obtained by detecting electrons using a detector in the positron emission tomography device;
  determine corresponding dimensional coordinates of the response line to be processed in a sinogram corresponding to the response line to be processed based on the first coordinate and the second coordinate; and
  generate the sinogram corresponding to the response line to be processed based on the dimensional coordinates and generate a positron emission tomography image based on the sinogram which is generated based on the dimensional coordinates.

In one embodiment, the processor is further configured to:
  obtain and store crystal coordinates and crystal numbers of a plurality of crystals from the positron emission tomography device;
  obtain a first crystal number and a second crystal number respectively corresponding to the two ends of the response line to be processed sent from the positron emission tomography device; and
  determine the first coordinate corresponding to the first crystal number, and determining the second coordinate corresponding to the second crystal number based on the crystal coordinates and the crystal numbers of the crystals, and the first crystal number and the second crystal number respectively corresponding to the two ends of the response line to be processed.

In one embodiment, the processor is further configured to:
  add a preset random number to the first coordinate and the second coordinate respectively to obtain a first continuous coordinate corresponding to the first coordinate and a second continuous coordinate corresponding to the second coordinate; and
  obtain the dimensional coordinates based on the first continuous coordinate and the second continuous coordinate.

In one embodiment, the processor is further configured to:
  determine a target response line corresponding to the response line to be processed based on the first continuous coordinate and the second continuous coordinate;
  project the target response line on a preset plane to obtain a projected response line;
  calculate a first dimensional coordinate and a second dimensional coordinate corresponding to the target response line based on the first continuous coordinate, the second continuous coordinate and the projected response line;
  calculate a third dimensional coordinate and a fourth dimensional coordinate corresponding to the target response line; and
  generate the dimensional coordinates based on the first dimensional coordinate, the second dimensional coordinate, the third dimensional coordinate, and the fourth dimensional coordinate.

In one embodiment, the processor is further configured to:
  calculate a vertical distance from the projected response line to a preset original point based on the first continuous coordinate and the second continuous coordinate;
  calculate an included angle formed between the projected response line and a preset horizontal direction based on the first continuous coordinate and the second continuous coordinate; and
  obtain the first dimensional coordinate and the second dimensional coordinate based on the vertical distance from the projected response line to the preset original point, and the included angle.

In one embodiment, the processor is further configured to perform a weighting processing on the response line generated based on the dimensional coordinates in the sinogram, based on the weighted value.

In one embodiment, the processor is further configured to:
  calculate a weighted value based on the first dimensional coordinate, the second dimensional coordinate, the third dimensional coordinate, and the fourth dimensional coordinate; and perform the weighting processing on the response line based on the weighted value.

In the third aspect, a non-transitory computer-readable storage medium is provided, this non-transitory computer-readable storage medium stores a computer program, that, when executed by a processor, causes the processor to the following steps of:
  obtaining a first coordinate and a second coordinate respectively corresponding to two ends of a response line to be processed from the positron emission tomography device, where the response line to be processed refers to a response line obtained by detecting electrons using a detector in the positron emission tomography device;

determining corresponding dimensional coordinates of the response line to be processed in a sinogram corresponding to the response line to be processed based on the first coordinate and the second coordinate; and generating the sinogram corresponding to the response line to be processed based on the dimensional coordinates, and generating a positron emission tomography image based on the sinogram which is generated based on the dimensional coordinates.

In the embodiments of the present application, the first coordinate and the second coordinate respectively corresponding to the two ends of the response line to be processed are obtained; the dimensional coordinate corresponding to the response line to be processed in the sinogram corresponding to the response line to be processed is determined based on the first coordinate and the second coordinate; and the sinogram corresponding to the response line to be processed is generated based on the dimensional coordinate. In this manner, the terminal device is used to obtain two coordinates corresponding to the two ends of the response line to be processed, and obtains the physical position of the response line to be processed by calculation based on the two coordinates, and generates the sinogram corresponding to the response line to be processed based on the dimensional coordinate corresponding to the response line to be processed. Due to the fact that the determined coordinates contain depth information of the response line to be processed, so that the PET device does not need to process the depth information in data processing process, the calculation amount of the system matrix is greatly reduced accordingly. The physical position of the response line to be processed obtained through this method is very accurate, so that the sinogram of the response line to be processed generated based on the dimensional coordinate is very accurate; furthermore, when the PET image is generated based on the sinogram, the resolution of the PET image generated based on the sinogram is high.

BRIEF DESCRIPTION OF THE DRAWINGS

In order to describe the technical solutions in the embodiments of the present application more clearly, a brief introduction regarding the accompanying drawings that need to be used in the description of the embodiments or the exemplary technology is given below; it is obvious that the accompanying figures described below are merely some embodiments of the present application, for the person of ordinary skill in the art, other drawings can also be obtained according to the current drawings without paying creative labor.

DETAILED DESCRIPTION

In order to make the objective, the technical solutions and the advantageous be clearer and more understandable, the present application is further described in detail with reference to the accompanying figures and the embodiments. It should be understood that, the embodiments described here are only used to explain the present application, rather than limiting the present application.

It needs to be noted that, when one component is described to be "fixed to" or "arranged on" another component, this component may be directly or indirectly arranged on another component. When it is described that one component "is connected with" another component, this component may be directly or indirectly connected to the another component. Orientation or position relationships indicated by terms including "upper", "lower", "left" and "right" are based on the orientation or position relationships shown in the accompanying figures and is only used for the convenience of description, instead of indicating or implying that the indicated device or element must have a specific orientation and is constructed and operated in a particular orientation, and thus should not be interpreted as limitation to the present application. For the person of ordinary skill in the art, the specific meanings of the aforesaid terms may be interpreted according to specific conditions. Terms of "the first" and "the second" are only for the purpose of describing conveniently and should not be interpreted as indicating or implying relative importance or implicitly indicating the number of indicated technical features. "Multiple/a plurality of" means two or more unless there is an additional explicit and specific limitation.

In order to describe the technical solutions of the present application, the present application is described with reference to the accompanying figures and the embodiments below.

Figure 1:
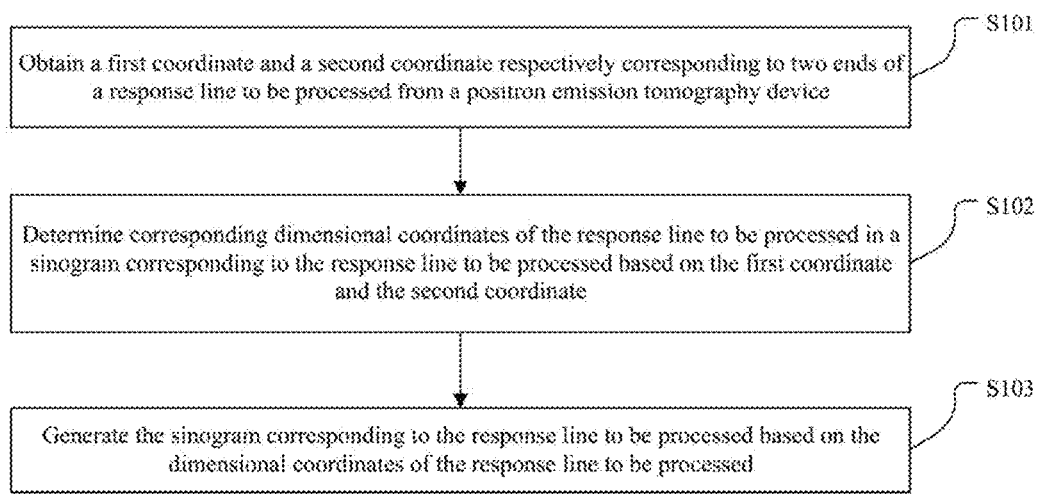
FIG. 1 illustrates a flowchart of implementation of a method for processing positron emission tomography according to one embodiment of the present application.

Referring to FIG. 1, FIG. 1 is a schematic flowchart of a method for processing PET (Positron Emission Tomography) data according to one embodiment of the present application. The execution subject of the method for processing the PET data in this embodiment is a terminal device 4, and this terminal device 4 includes but is not limited to a mobile terminal such as a smart phone, a tablet computer, a PDA (Personal Digital Assistant), or the like, and may also include a terminal device 4 such as a desktop computer. The method for processing the PET data as shown in FIG. 1 may include:

At step S101, a first coordinate and a second coordinate respectively corresponding to two ends of a response line to be processed are obtained.

The first coordinate and the second coordinate respectively corresponding to two ends of the response line to be processed are obtained by the terminal device 4. The response line to be processed refers to a response line obtained by detecting electrons using a detector in a PET device. As shown in the PET device in FIG. 2, the detector is composed of four rings, each ring is consisted of 12 modules, and each module is consisted of 529 crystals, and each of the crystals has a corresponding crystal coordinate and a crystal number. When a annihilation reaction is generated between a positron and an electron, a pair of back-to-back gamma photon pairs are generated, the energies of the pair of gamma photon pairs are equal to 511 KeV, and the directions of the pair of gamma photon pairs are opposite and form an angle of about 180 degrees, the two electrons are respectively punched on two crystals of the detector and are recorded by the PET device, and a connecting line of the two crystals are one response line.

The PET device sends the data corresponding to the response line to the terminal device 4; for example, the PET device sends the crystal numbers of the two crystals at the two ends of the response line to the terminal device 4. The terminal device 4 obtains and stores the crystal coordinates and the crystal numbers of the crystals in the PET device previously; when the crystal numbers corresponding to the two ends of the response line to be processed sent by the PET device are received, the first coordinate and the second coordinate of the two crystals corresponding to the two ends of the response line to be processed are searched in the prestored crystal coordinates and coordinate numbers corresponding to the crystals.

Furthermore, in order to accurately obtain the coordinates corresponding to the two ends of the response line to be processed, the step S101 may include a step S1011, a step S1012 and a step S1013, these steps are In particular described below:

At step S1011, the crystal coordinates and the crystal numbers corresponding to the crystals in the PET device are obtained.

Figure 2:
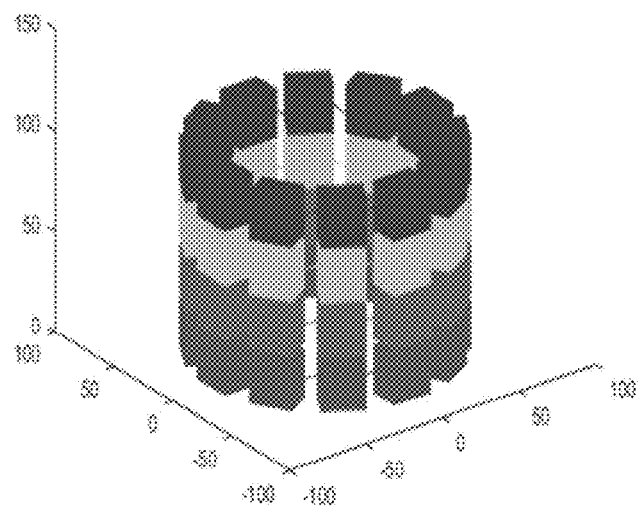
FIG. 2 illustrates a schematic diagram of a detector of a device for processing positron emission tomography data according to the present application.

The terminal device 4 obtains the crystal coordinates and the crystal numbers corresponding to the crystals in the PET device. In particular, FIG. 2 shows a detector of the PET device, a coordinate system is established for the crystals in the detector, coordinates of the crystals in the X direction, the Y direction and the Z direction in the PET device are determined, so that the coordinates of the crystals are obtained; where the Z coordinate may represent a crystal ring number corresponding to the crystal. Corresponding crystal numbers are preset for the crystals, and the terminal device 4 associates the crystal coordinates of the crystals with the crystal numbers of the crystals and stores the crystal coordinates and the crystal numbers that are associated. In order to facilitate the terminal device 4 to extract the coordinates corresponding to the two ends of the response line to be processed respectively, the crystal coordinates and the crystal numbers corresponding to the crystals may be stored in a matrix form; for example, the coordinates of the crystals in the X direction, in the Y direction and in the Z direction are stored as X matrix, Y matrix, and Z matrix, and the below of each coordinate in each matrix is labeled with a crystal number corresponding to the coordinate.

At step S1012, the first crystal number and the second crystal number respectively corresponding to the two ends of the response line to be processed are obtained.

The PET device sends the data corresponding to the response line to be processed to the terminal device 4. For example, the PET device sends the first crystal number and the second crystal number of the two crystals at the two ends of the response line to be processed to the terminal device 4 in a list form; and the terminal device 4 receives the first crystal number and the second crystal number of the two crystals at the two ends of the response line to be processed, which is sent by the PET device.

At step S1013, the first coordinate corresponding to the first crystal number, and the second coordinate corresponding to the second crystal number are determined based on the crystal coordinates and the crystal numbers corresponding to the crystals respectively.

The crystal coordinates and the crystal numbers corresponding to the crystals in the terminal device 4 are prestored in the PET device, when the first crystal number and the second crystal number respectively corresponding to the two crystals at the two ends of the response line to be processed are obtained, a crystal corresponding to the crystal number matched with the first crystal number is searched out in the prestored crystal numbers, then, the crystal coordinate corresponding to this crystal is obtained, so that the first coordinate corresponding to the first crystal number is obtained. Similarly, a crystal corresponding to the crystal number matched with the second crystal number is searched out in the prestored crystal numbers, then, the crystal coordinate corresponding to this crystal is obtained, so that the second coordinate corresponding to the second crystal number is obtained. For example, the first coordinate and the second coordinate corresponding to the two crystals at the two ends of the response line to be processed is $(X_1,Y_1,Z_1)$ and $(X_2,Y_2,Z_2)$, respectively.

At step S102, a corresponding dimensional coordinate of the response line to be processed in a sinogram to be generated is determined based on the first coordinate and the second coordinate.

The terminal device 4 calculates a corresponding dimensional coordinate of the response line to be processed in the sinogram corresponding to the response line to be processed based on the first coordinate and the second coordinate. Finally, the terminal device 4 generates the sinogram corresponding to the response line to be processed, and the dimensional coordinate is the coordinate corresponding to the response line to be processed in the sinogram to be processed. It may also be understood that, after the sinogram corresponding to the response line to be processed is generated, the dimensional coordinate is the coordinate corresponding to the response line to be processed in the generated sinogram.

A preset random number is added to the first coordinate and the second coordinate of the response line to be processed respectively to obtain a first continuous coordinate corresponding to the first coordinate and a second continuous coordinate corresponding to the second coordinate; and a target response line corresponding to the response line to be processed is determined according to the first continuous coordinate and the second continuous coordinate; the target response line is projected on a preset plane to obtain a projected response line; a first dimensional coordinate and a second dimensional coordinate corresponding to the target response line are determined based on the first continuous coordinate, the second continuous coordinate and the projected response line; a third dimensional coordinate and a fourth dimensional coordinate corresponding to the target response line are determined; and the dimensional coordinate is generated based on the first dimensional coordinate, the second dimensional coordinate, the third dimensional coordinate, and the fourth dimensional coordinate.

Furthermore, in order to accurately calculate the coordinates of the response line to be processed in the sinogram corresponding to the response line to be processed, the step S102 may include a step 1021 and a step S1022, the step S1021 and the step S1022 are described in detail below:

At step S1021, a preset random number is added to the first coordinate and the second coordinate respectively to obtain a first continuous coordinate corresponding to the first coordinate and a second continuous coordinate corresponding to the second coordinate.

The terminal device 4 adds the preset random number into the first coordinate and the second coordinate of the response line to be processed to obtain the first continuous coordinate corresponding to the first coordinate and the second continuous coordinate corresponding to the second coordinate. In particular, the preset random number is preset by a user; for example, the user may set the preset random number according to different depth information contained in the crystals in the PET device, the setting of the preset random number is not limited herein. The terminal device 4 adds the preset random number into the coordinates in various directions respectively in the first coordinate and the second coordinate, and the obtained results are recorded as the first continuous coordinate and the second continuous coordinate, respectively. For example, the first coordinate is represented by $(X_1,Y_1,Z_1)$, the second coordinate is represented by $(X_2,Y_2,Z_2)$ the random number is respectively added to the first coordinate and the second coordinate to obtain the first continuous coordinate represented by $(x_1,y_1,z_1)$ and the second continuous coordinate represented by $(x_2,y_2,z_2)$. By adding the preset random number to the first coordinate and the second coordinate, so that the representation of the position of the response line to be processed is more accurate, and the subsequently generated sinogram is more accurate.

At step S1022, the dimensional coordinate is determined based on the first continuous coordinate and the second continuous coordinate.

The dimensional coordinate is determined by the terminal device 4 based on the first continuous coordinate and the second continuous coordinate. In particular, the terminal device 4 may determine a response line according to the first continuous coordinate and the second continuous coordinate and project this response line onto a preset plane; for example, the response line is projected onto a horizontal plane corresponding to the detector in the PET device to obtain a projected response line corresponding to the response line. A first dimensional coordinate and a second dimensional coordinate corresponding to the determined response line according to the first continuous coordinate, the second continuous coordinate and the projected response line; a third dimensional coordinate and a fourth dimensional coordinate corresponding to the determined response line are determined; and the corresponding dimensional coordinates of the response line to be processed in the sinogram corresponding to the response line to be processed is generated based on the first dimensional coordinate, the second dimensional coordinate, the third dimensional coordinate and the fourth dimensional coordinate.

Furthermore, in order to accurately calculate the dimensional coordinates, and make the determined dimensional coordinates to reflect a physical position of the response line to be processed in the sinogram more accurately, the step S1022 may include step S10221, step S10222, step S10223, step S10224 and step S10225, these steps are described in detail below:

At step S10221, the target response line corresponding to the response line to be processed is determined based on the first continuous coordinate and the second continuous coordinate.

The target response line corresponding to the response line to be processed is determined by the terminal device 4 based on the first continuous coordinate and the second continuous coordinate. In particular, the terminal device 4 may determine a target response line according to the two coordinate points (i.e., the first continuous coordinate and the second continuous coordinate), and the target response line which is obtained by repositioning corresponds to the response line to be processed.

At step S10222, the target response line is projected on a preset plane to obtain the projected response line.

Figure 3:
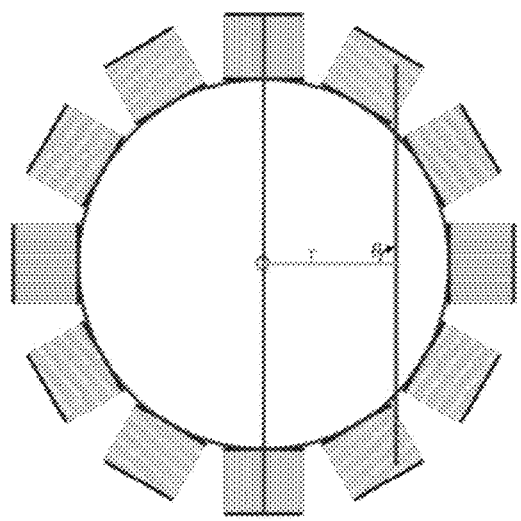
FIG. 3 illustrates a schematic diagram of a projection corresponding to the response line to be processed according to the present application.

The terminal device 4 projects the target response line on the preset plane to obtain the projected response line. For example, the target response line is projected on a horizontal plane corresponding to the detector in the PET device, so that the projected response line corresponding to the target response line is obtained. As shown in FIG. 3, a shorter line segment on the right side is the projected response line obtained by projecting the target response line on the horizontal plane corresponding to the detector in the PET device.

At step S10223, the first dimensional coordinate and the second dimensional coordinate corresponding to the target response line are determined based on the first continuous coordinate, the second continuous coordinate and the projected response line.

The first dimensional coordinate and the second dimensional coordinate corresponding to the target response line are obtained by the terminal device 4 according to the first continuous coordinate, the second continuous coordinate and the projected response line. In particular, a vertical distance from the projected response line to a preset origin and an included angle formed between the projected response line and the preset horizontal direction are determined by the terminal device 4; as an alternative, a vertical distance from the projected response line to a preset line segment is determined by the terminal device 4, as shown in FIG. 3, the shorter line segment at the right side is the projected response line, and the longer line segment at the left side is the preset line segment, and the vertical distance from the projected response line to the preset line segment is determined by the terminal device 4. The first dimensional coordinate and the second dimensional coordinate corresponding to the target response line are determined by the terminal device 4 according to the determined vertical distance and the included angle.

Furthermore, in order to calculate the dimensional coordinates accurately, in order that the determined dimensional coordinates can reflect the physical position of the response line to be processed in the sinogram corresponding to the response line to be processed more accurately, the step S10223 may include a step S102231, a step S102232 and a step S102233, these steps are described in detail below:

At step S102231, a vertical distance from the projected response line to a preset origin is determined based on the first continuous coordinate and the second continuous coordinate.

The vertical distance from the projected response line to the preset origin is determined by the terminal device 4 according to the first continuous coordinate and the second continuous coordinate. In particular, a distance r between the projected response line and the preset origin (0,0) is determined by the terminal device 4, and the distance r may be determined by using a distance formula for calculating a distance from point to straight line. This formula is expressed as follows:

$$r = \frac{y_1(x_1 - x_2) - x_1(y_1 - y_2)}{\sqrt{(y_1 - y_2)^2 + (x_1 - x_2)^2}}$$

At Step S102232, the included angle formed between the projected response line and the preset horizontal direction is determined by the terminal device 4 based on the first continuous coordinate and the second continuous coordinate.

The included angle formed between the projected response line and the preset horizontal direction is determined by the terminal device 4 based on the first continuous coordinate and the second continuous coordinate. In particular, a X coordinate and a Y coordinate in the first continuous coordinate, and a X coordinate and a Y coordinate in the second continuous coordinate are obtained by the terminal device 4; the included angle formed between the projected response line and the preset horizontal direction is determined based on a formula expressed as $$\theta = \arctan\left(\frac{y_1 - y_2}{x_1 - x_2}\right) + \pi.$$

Where θ represents the included angle formed between the projected response line and the preset horizontal direction, $(x_1, y_1)$ and $(x_2, y_2)$ represent coordinates in the X direction and the Y direction in the first continuous coordinate and the second continuous coordinate, respectively.

At step S102233, the first dimensional coordinate and the second dimensional coordinate are determined based on the vertical distance and the included angle.

The first dimensional coordinate and the second dimensional coordinate are determined by the terminal device 4 based on the vertical distance and the included angle. In particular, the first dimensional coordinate and the second dimensional coordinate are determined based on a formula expressed as $$sx = \left[\frac{\theta}{\pi/na}\right], sy = \left[\frac{r}{bs}\right] + \frac{nr}{2};$$

where sx represents the first dimensional coordinate, sy represents the second dimensional coordinate, θ represents the included angle formed between the projected response line and the preset horizontal direction, na represents a size of the first dimension of the sinogram corresponding to the response line to be processed, nr represents a size of the second dimension of the sinogram corresponding to the response line to be processed, bs is preset by the user, bs may be one-half or one third of a size of a crystal in the PET device. The more accurate the value of bs, the higher the resolution of the finally generated PET image.

At step S10224, the third dimensional coordinate and the fourth dimensional coordinate corresponding to the target response line are determined by the terminal device 4.

Figure 4:
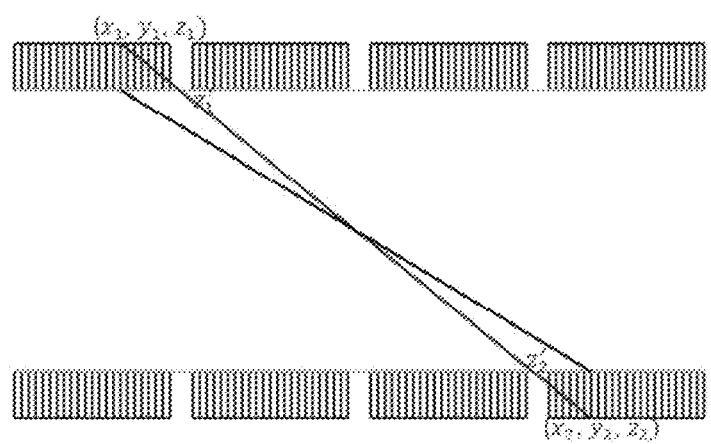
FIG. 4 illustrates coordinates corresponding to the response line to be processed according to the present application.

The third dimensional coordinate and the fourth dimensional coordinate corresponding to the target response line are determined by the terminal device 4. In particular, as shown in FIG. 4, the coordinates corresponding to intersection points $z_1'$, $z_2'$ of a longer line segment in the graph and two parallel lines are the third dimensional coordinate and the fourth dimensional coordinate corresponding to the target response line. The third dimensional coordinate and the fourth dimensional coordinate may be determined by solving an equation, wherein the equation set is expressed as follows:

$$\begin{cases} x = x_1 + (z - z_1)(x_2 - x_1)/(z_2 - z_1) \\ y = y_1 + (z - z_1)(y_2 - y_1)/(z_2 - z_1) \\ x^2 + y^2 = R^2 \end{cases}$$

where, $(x_1, y_1, z_1)$ represents the third dimensional coordinate, $(x_2, y_2, z_2)$ represents the fourth dimensional coordinate; R is a radius of the detector in the PET device; this equation set is solved, so that the third dimensional coordinate and the fourth dimensional coordinate are obtained.

At step S10225, the corresponding dimensional coordinates of the response line in the sinogram corresponding to the response line to be processed are generated based on the first dimensional coordinate, the second dimensional coordinate, the third dimensional coordinate, and the fourth dimensional coordinate.

The corresponding dimensional coordinates of the response line in the sinogram corresponding to the response line to be processed are generated by the terminal device 4 based on the first dimensional coordinate, the second dimensional coordinate, the third dimensional coordinate, and the fourth dimensional coordinate. The terminal device 4 combines the first dimensional coordinate, the second dimensional coordinate, the third dimensional coordinate and the fourth dimensional coordinate which are obtained by calculation, and records the combined coordinates as the corresponding dimensional coordinates of the response line to be processed in the sinogram corresponding to the response line to be processed.

At step S103, the sinogram corresponding to the response line to be processed is generated by the terminal device 4 based on the dimensional coordinates.

The terminal device 4 generates the sinogram corresponding to the response line to be processed based on the dimensional coordinates. In particular, the corresponding points in the sinogram corresponding to the response line to be processed are drawn according to the dimensional coordinates, and the sinogram corresponding to the response line to be processed is obtained after drawing of the points corresponding to the dimensional coordinates in the sinogram corresponding to the response line to be processed is completed.

In this embodiment, the dimensional coordinates determined by the terminal device 4 may represent the physical position of the response line to be processed in the sinogram corresponding to the response line to be processed, the sinogram which corresponds to the response line to be processed and is generated based on the dimensional coordinates may reflect the depth information of the response line to be processed; when the data is processed by the PET device, the depth information needs not to be processed, so that a calculation amount of the system matrix is greatly reduced.

Furthermore, all obtained response lines to be processed are processed by the terminal device 4 according to the method for processing PET data, when all response lines to be processed have been processed, all sinograms corresponding to the response lines to be processed are combined to generate a sinogram that is finally required by the user; the PET image is generated according to this sinogram, so that the generated PET image has a high resolution; since the actually obtained coordinates include depth information corresponding to the response line to be processed, so that the PET device does not need to process the depth information when data is processed, and the calculation amount of the system matrix is greatly reduced.

According to this embodiment of the present application, the first coordinate and the second coordinate respectively corresponding to the two ends of the response line to be processed are obtained; the corresponding dimensional coordinate of the response line to be processed in the sinogram to be processed is determined based on the first coordinate and the second coordinate; and a sinogram corresponding to the response line to be processed is generated based on the dimensional coordinate. According to this method, two coordinates corresponding to the two ends of the response line to be processed are obtained by the terminal device 4, and the physical position of the response line to be processed is determined based on the two coordinates, and the sinogram corresponding to the response line to be processed is generated based on the dimensional coordinates corresponding to the response line to be processed. Due to the fact that the actually obtained coordinates include depth information corresponding to the response line to be processed, so that the PET device does not need to process the depth information, and the calculation amount of the system matrix is greatly reduced. The physical position of the response line to be processed obtained according to this method is very accurate, so that the generated sinogram corresponding to the response line to be processed is very accurate; furthermore, when the PET image is generated based on the sinogram, the resolution of the PET image generated based on the sinogram is high.

Figure 5:
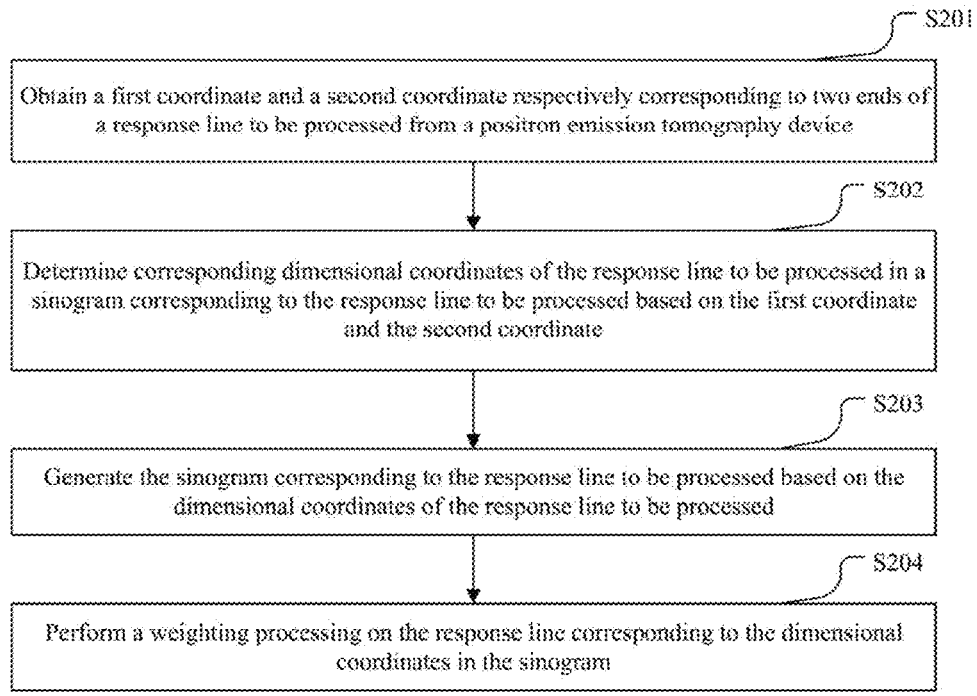
FIG. 5 illustrates a flowchart of implementation of a method for processing positron emission tomography according to another embodiment of the present application.

Referring to FIG. 5, FIG. 5 is a schematic flowchart of a method for processing PET (Positron Emission Tomography) data according to another embodiment of the present application. The executive subject of the method for processing PET data in this embodiment is a terminal device 4, this terminal device 4 includes but is not limited to a mobile terminal such as a smart phone, a tablet computer, a personal digital assistant, and the like, the terminal device 4 may also be such as a desktop computer.

The difference between this embodiment and the previously described embodiment is the step S204. The steps S201-S203 in this embodiment are completely the same as the steps S101-S103 in the previously described embodiment, regarding the details of the steps S201-S203, reference can be made to the related descriptions of the steps S101-S103 in the previously described embodiment, the details of the steps S201-S203 are not repeatedly described herein.

Furthermore, in order to more accurately determine the physical position of the response line to be processed to enable the generated sinogram to be more accurate, the method may further include the step S204 after the step S203, the step S204 is described in detail below:

At step S204, a weighting processing is performed on the response line corresponding to the dimensional coordinates in the sinogram.

The weighting processing is performed on the response line corresponding to the dimensional coordinate in the sinogram by the terminal device 4. In particular, a weighted value is determined by the terminal device 4 according to the first dimensional coordinate, the second dimensional coordinate, the third dimensional coordinate, and the fourth dimensional coordinate; values are assigned to 16 positions corresponding to the response line in the sinogram based on the weighted value, and the sum of the increase of the values of the 16 positions is 1. It should be understood that, one response line may affect 16 cells in the sinogram, values of the 16 cells are increased according to the weighted value, and the sum of the increased values of the 16 cells is 1. In other words, one response line affects a plurality of position units in the sinogram, value are assigned to the position cells according to the weighted value, so that the sum of change values of all position units affected by one single response line is 1.

Furthermore, in order to perform weighting processing accurately, the step S204 may include steps S2041-S2042 which are described in detail below:

At step S2041, the weighted value is determined based on the first dimensional coordinate, the second dimensional coordinate, the third dimensional coordinate, and the fourth dimensional coordinate.

The weighted value is determined by the terminal device 4 according to the first dimensional coordinate, the second dimensional coordinate, the third dimensional coordinate, and the fourth dimensional coordinate. The terminal device 4 calculates the weighted value through a following formula listed below:

$$wx = \frac{\theta}{\pi/na} - \left[\frac{\theta}{\pi/na}\right], wy = \frac{r}{bs} - \left[\frac{r}{bs}\right], w_{z_1} = z'_1 - [z'_1], w_{z_2} = z'_2 - [z'_2];$$

Where, wx represents the weighted value corresponding to the first dimension, wy represents the weighted value corresponding to the second dimension, $w_{z_1}$ represents the weighted value corresponding to the third dimension, and $w_{z_2}$ represents the weighted value corresponding to the fourth dimension.

At step S2042, the weighting processing is performed on the response line corresponding to the dimensional coordinates based on the weighted value.

The weighting processing is performed on the response line corresponding to the dimensional coordinate based on the weighted value. In particular, values are assigned to the values of 16 positions corresponding to the response line in the sinogram based on the weighted value, and the sum of the increased values of the 16 positions is 1. It should be understood that, one response line may affect 16 cells in the sinogram, values of the 16 cells are increased according to the weighted value, and the sum of the increased values of the 16 cells is 1. In other words, one response line affects a plurality of position units in the sinogram, values are assigned to the position cells according to the weighted value, so that the sum of change values of all position units affected by one single response line is 1. When the response line is imported into the sinogram by the terminal device 4, values are assigned to elements in the sinogram according to the determined weighted values. The terminal device 4 implements weighting processing based on the formula listed below:

$(sx,sy,sz_1,sz_2)=(1-w_x)(1-w_y)(1-w_{z_1})(1-w_{z_2})$ $(sx+1,sy,sz_1,sz_2)=w_x(1-w_y)(1-w_{z_1})(1-w_{z_2})$ $(sx,sy+1,sz_1,sz_2)=(1-w_x)w_y(1-w_{z_1})(1-w_{z_2})$ $(sx,sy,sz_1+1,sz_2)=(1-w_x)(1-w_y)w_{z_1}(1-w_{z_2})$ $(sx,sy,sz_1,sz_2+1)=(1-w_x)(1-w_y)(1-w_{z_1})w_{z_2}$ $(sx+1,sy+1,sz_1,sz_2)=w_xw_y(1-w_{z_1})(1-w_{z_2})$ $(sx+1,sy,sz_1+1,sz_2)=w_x(1-w_y)w_{z_1}(1-w_{z_2})$ $(sx+1,sy,sz_1,sz_2+1)=w_x(1-w_y)(1-w_{z_1})w_{z_2}$ $$(sx, sy+1, sz_1+1, sz_2) = (1-w_x)w_y w_{z_1}(1-w_{z_2})$$

$$(sx, sy+1, sz_1, sz_2+1) = (1-w_x)w_y(1-w_{z_1})w_{z_2}$$

$$(sx, sy, sz_1+1, sz_2+1) = (1-w_x)(1-w_y)w_{z_1}w_{z_2}$$

$$(sx+1, sy+1, sz_1+1, sz_2) = w_x w_y w_{z_1}(1-w_{z_2})$$

$$(sx+1, sy+1, sz_1, sz_2+1) = w_x w_y(1-w_{z_1})w_{z_2}$$

$$(sx, sy+1, sz_1+1, sz_2+1) = (1-w_x)w_y w_{z_1}w_{z_2}$$

$$(sx+1, sy, sz_1+1, sz_2+1) = w_x(1-w_y)w_{z_1}w_{z_2}$$

$$(sx+1, sy+1, sz_1+1, sz_2+1) = w_x w_y w_{z_1}w_{z_2}$$

According to the embodiment of the present application, the first coordinate and the second coordinate respectively corresponding to the two ends of the response line to be processed are obtained; based on the first coordinate and the second coordinate, the corresponding dimensional coordinate of the response line to be processed in the to-be-processed sinogram is determined; and the sinogram corresponding to the response line to be processed is generated based on the dimensional coordinates. In the above manner, two coordinates corresponding to the two ends of the response line to be processed are acquired by the terminal, and the physical position of the response line to be processed is determined based on the two coordinates, and the sinogram corresponding to the response line to be processed is generated based on the dimensional coordinates corresponding to the response line to be processed. Since the determined actual coordinates contain depth information corresponding to the response line to be processed, so that the PET device does not need to process the depth information, and the calculation amount of the system matrix is reduced to a great extent; the obtained physical position of the response line to be processed is very accurate, so that the generated sinogram corresponding to the response line to be processed is very accurate. Furthermore, the weighting processing is performed to further correct the physical position of the response line to be processed based on the determined dimensional coordinates, so that the generated sinogram corresponding to the response line to be processed is more accurate; when the PET image is generated based on this sinogram, the PET image generated based on the sinogram has a higher resolution and a higher definition.

Figure 6:
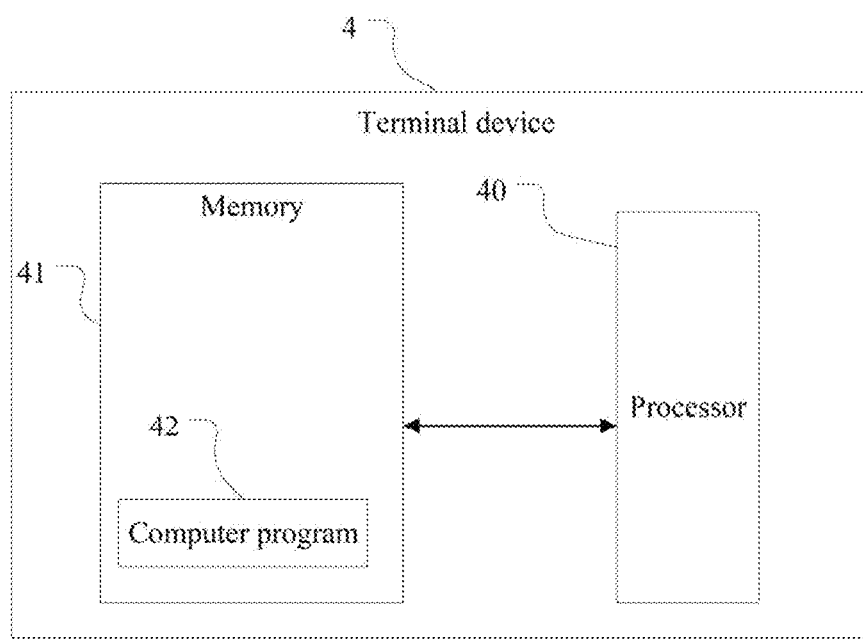
FIG. 6 illustrates a schematic structural diagram of a terminal device for processing positron emission tomography data provided by another embodiment of the present application.

Referring to FIG. 6, FIG. 6 is a schematic diagram of a terminal device 4 for processing PET (Positron Emission Tomography) data according to another embodiment of the present application. As shown in FIG. 6, the terminal device 4 of this embodiment includes: a processor 40, a memory 41 and a computer program 42 stored in the memory 41 and executable on the processor 40. When the computer program 42 is executed by the processor 40, the steps in the method embodiments of processing PET data, such as the steps S101, the step S102, the step S103 shown in FIG. 1, are implemented.

The terminal device 4 may include but is not limited to the processor 40 and the memory 41. A person of ordinary skill in the art can understand that, FIG. 6 is only one example of the terminal device 4, and should not be constituted as limitation to the terminal device 4, the terminal device 4 may more or less components than the components shown in FIG. 6, as an alternative, some components or different components may be combined into the terminal device 4; for example, the terminal device 4 may also include an input and output device, a network access device, etc.

The so-called processor 40 may be CPU (Central Processing Unit), and may also be other general purpose processor, DSP (Digital Signal Processor), ASIC (Application Specific Integrated Circuit), FGPA (Field-Programmable Gate Array), or some other programmable logic devices, discrete gate or transistor logic device, discrete hardware component, etc. The general purpose processor may be a microprocessor, as an alternative, the processor 40 may also be any conventional processor, and the like.

The memory 41 may be an internal storage unit of the terminal device 4, the internal storage unit may be such as a hard disk or a memory of the terminal device 4. The memory 41 may also be an external storage device of the terminal device 4, the external storage device may be such as a plug-in hard disk, a SMC (Smart Media Card), a SD (Secure Digital) card, a FC (Flash Card) equipped on the terminal device 4. Furthermore, the memory 41 may not only include the internal storage unit of the terminal device 4, but also include the external memory of the terminal device 4. The memory 41 is configured to store the computer program, and other procedures and data needed by the terminal device 4. The memory 41 may also be configured to store data that has been output or being ready to be output temporarily.

The aforesaid embodiments are only intended to explain but not to limit the technical solutions of the present application. Although the present application has been explained in detail with reference to these embodiments, a person of ordinary skilled in the art can understand that, the technical solutions disclosed in the embodiments can also be amended, some technical features in the technical solutions can also be equivalently replaced; the amendments or the equivalent replacements don't cause the essence of the corresponding technical solutions to be deviated from the spirit and the scope of the technical solutions in the embodiments of the present application, and thus should all be included in the protection scope of the present application.

What is claimed is:

1. A method for processing positron emission tomography data implemented by a terminal device, comprising:
   obtaining a first coordinate and a second coordinate respectively corresponding to two ends of a response line to be processed from a positron emission tomography device, wherein the response line to be processed refers to a response line obtained by detecting electrons using a detector in the positron emission tomography device;
   determining corresponding dimensional coordinates of the response line to be processed in a sinogram corresponding to the response line to be processed based on the first coordinate and the second coordinate; and
   generating the sinogram corresponding to the response line to be processed based on the dimensional coordinates, and generating a positron emission tomography image based on the sinogram generated based on the dimensional coordinates;
   wherein after said generating the sinogram corresponding to the response line to be processed based on the dimensional coordinates, the method further comprises:
   performing a weighting processing on the response line generated based on the dimensional coordinates in the sinogram.

2. The method of claim 1, wherein said obtaining the first coordinate and the second coordinate respectively corresponding to the two ends of the response line to be processed from the positron emission tomography device comprises:

obtaining and storing crystal coordinates and crystal numbers of a plurality of crystals from the positron emission tomography device;

obtaining a first crystal number and a second crystal number respectively corresponding to the two ends of the response line to be processed sent from the positron emission tomography device; and determining the first coordinate corresponding to the first crystal number and determining the second coordinate corresponding to the second crystal number based on the crystal coordinates and the crystal numbers of the plurality of crystals, and the first crystal number and the second crystal number respectively corresponding to the two ends of the response line to be processed.

3. The method of claim 1, wherein said determining the dimensional coordinates of the response line to be processed in the sinogram corresponding to the response line to be processed comprises:

adding a preset random number to the first coordinate and the second coordinate respectively to obtain a first continuous coordinate corresponding to the first coordinate and a second continuous coordinate corresponding to the second coordinate; and obtaining the dimensional coordinates based on the first continuous coordinate and the second continuous coordinate.

4. The method of claim 3, wherein said obtaining the dimensional coordinates based on the first continuous coordinate and the second continuous coordinate comprises:

determining a target response line corresponding to the response line to be processed based on the first continuous coordinate and the second continuous coordinate;

projecting the target response line on a preset plane to obtain a projected response line;

determining a first dimensional coordinate and a second dimensional coordinate corresponding to the target response line based on the first continuous coordinate, the second continuous coordinate and the projected response line;

determining a third dimensional coordinate and a fourth dimensional coordinate corresponding to the target response line; and generating the dimensional coordinates based on the first dimensional coordinate, the second dimensional coordinate, the third dimensional coordinate, and the fourth dimensional coordinate.

5. The method of claim 4, wherein said determining the first dimensional coordinate and the second dimensional coordinate corresponding to the target response line based on the first continuous coordinate, the second continuous coordinate and the projected response line comprises:

determining a vertical distance from the projected response line to a preset original point based on the first continuous coordinate and the second continuous coordinate;

determining an included angle formed between the projected response line and a preset horizontal direction based on the first continuous coordinate and the second continuous coordinate; and obtaining the first dimensional coordinate and the second dimensional coordinate based on the vertical distance from the projected response line to the preset original point, and the included angle.

6. The method of claim 1, wherein said performing weighting processing on the response line generated based on the dimensional coordinates in the sinogram comprises:

determining a weighted value based on the first dimensional coordinate, the second dimensional coordinate, the third dimensional coordinate, and the fourth dimensional coordinate; and performing, based on the weighted value, the weighting processing on the response line generated based on the dimensional coordinates.

7. A terminal device for processing positron emission tomography data, comprising a memory, a processor and a computer program stored in the memory and executable by the processor, wherein the processor is configured to execute the computer program so as to:

obtain a first coordinate and a second coordinate respectively corresponding to two ends of a response line to be processed from a positron emission tomography device, wherein the response line to be processed refers to a response line obtained by detecting electrons using a detector in the positron emission tomography device;

determine corresponding dimensional coordinates of the response line to be processed in a sinogram corresponding to the response line to be processed based on the first coordinate and the second coordinate; and generate the sinogram corresponding to the response line to be processed based on the dimensional coordinates and generate a positron emission tomography image based on the sinogram which is generated based on the dimensional coordinates;

wherein the processor is further configured to perform, based on the weighted value, a weighting processing on the response line generated based on the dimensional coordinates in the sinogram.

8. The terminal device of claim 7, wherein the processor is further configured to:

obtain and store crystal coordinates and crystal numbers of a plurality of crystals from the positron emission tomography device;

obtain a first crystal number and a second crystal number respectively corresponding to the two ends of the response line to be processed sent from the positron emission tomography device; and determine the first coordinate corresponding to the first crystal number, and determine the second coordinate corresponding to the second crystal number based on the crystal coordinates and the crystal numbers of the plurality of crystals and the first crystal number and the second crystal number respectively corresponding to the two ends of the response line to be processed.

9. The terminal device of claim 7, wherein the processor is further configured to:

add a preset random number to the first coordinate and the second coordinate respectively to obtain a first continuous coordinate corresponding to the first coordinate and a second continuous coordinate corresponding to the second coordinate; and obtain the dimensional coordinates based on the first continuous coordinate and the second continuous coordinate.

10. A non-transitory computer-readable storage medium which stores a computer program, that, when executed by a processor, causes the processor to implement following steps, comprising:

obtaining a first coordinate and a second coordinate respectively corresponding to two ends of a response line to be processed from a positron emission tomography device, wherein the response line to be processed refers to a response line obtained by detecting electrons using a detector in the positron emission tomography device;

determining corresponding dimensional coordinates of the response line to be processed in a sinogram corresponding to the response line to be processed based on the first coordinate and the second coordinate; and generating the sinogram corresponding to the response line to be processed based on the dimensional coordinates and generating a positron emission tomography image based on the sinogram which is generated based on the dimensional coordinates;

wherein after said generating the sinogram corresponding to the response line to be processed based on the dimensional coordinates, performing a weighting processing on the response line generated based on the dimensional coordinates in the sinogram.

11. The non-transitory computer-readable storage medium of claim 10, wherein the computer program is further configured to, when executed by the processor, causes the processor to implement the step of obtaining the first coordinate and the second coordinate respectively corresponding to the two ends of the response line to be processed, by:

obtaining and storing crystal coordinates and crystal numbers of a plurality of crystals in a positron emission tomography device from the positron emission tomography device;

obtaining a first crystal number and a second crystal number respectively corresponding to the two ends of the response line to be processed sent from the positron emission tomography device; and determining the first coordinate corresponding to the first crystal number and determining the second coordinate corresponding to the second crystal number based on the crystal coordinates and the crystal numbers of the plurality of crystals and the first crystal number and the second crystal number respectively corresponding to the two ends of the response line to be processed.

12. The non-transitory computer-readable storage medium of claim 10, wherein the computer program is further configured to, when executed by the processor, causes the processor to implement the step of determining the dimensional coordinates of the response line to be processed in the sinogram corresponding to the response line to be processed, by:

adding a preset random number to the first coordinate and the second coordinate respectively to obtain a first continuous coordinate corresponding to the first coordinate and a second continuous coordinate corresponding to the second coordinate; and obtaining the dimensional coordinates based on the first continuous coordinate and the second continuous coordinate.

13. The terminal device of claim 9, wherein the processor is further configured to:

determine a target response line corresponding to the response line to be processed based on the first continuous coordinate and the second continuous coordinate;

project the target response line on a preset plane to obtain a projected response line;

calculate a first dimensional coordinate and a second dimensional coordinate corresponding to the target response line based on the first continuous coordinate, the second continuous coordinate and the projected response line;

calculate a third dimensional coordinate and a fourth dimensional coordinate corresponding to the target response line; and generate the dimensional coordinates based on the first dimensional coordinate, the second dimensional coordinate, the third dimensional coordinate, and the fourth dimensional coordinate.

14. The terminal device of claim 13, wherein the processor is further configured to:

calculate a vertical distance from the projected response line to a preset original point based on the first continuous coordinate and the second continuous coordinate;

calculate an included angle formed between the projected response line and a preset horizontal direction based on the first continuous coordinate and the second continuous coordinate; and obtain the first dimensional coordinate and the second dimensional coordinate based on the vertical distance from the projected response line to the preset original point, and the included angle.

15. The terminal device of claim 7, wherein the processor is further configured to:

calculate a weighted value based on the first dimensional coordinate, the second dimensional coordinate, the third dimensional coordinate, and the fourth dimensional coordinate; and performing the weighting processing on the response line based on the weighted value.

16. The non-transitory computer-readable storage medium of claim 10, wherein the computer program is further configured to, when executed by the processor, causes the processor to implement the step of obtaining the dimensional coordinates based on the first continuous coordinate and the second continuous coordinate, by:

determining a target response line corresponding to the response line to be processed based on the first continuous coordinate and the second continuous coordinate;

projecting the target response line on a preset plane to obtain a projected response line;

determining a first dimensional coordinate and a second dimensional coordinate corresponding to the target response line based on the first continuous coordinate, the second continuous coordinate and the projected response line;

determining a third dimensional coordinate and a fourth dimensional coordinate corresponding to the target response line; and generating the dimensional coordinates based on the first dimensional coordinate, the second dimensional coordinate, the third dimensional coordinate, and the fourth dimensional coordinate.

17. The non-transitory computer-readable storage medium of claim 16, wherein the computer program is further configured to, when executed by the processor, causes the processor to implement the step of determining the first dimensional coordinate and the second dimensional coordinate corresponding to the target response line based on the first continuous coordinate, the second continuous coordinate and the projected response line, by:

determining a vertical distance from the projected response line to a preset original point based on the first continuous coordinate and the second continuous coordinate;

determining an included angle formed between the projected response line and a preset horizontal direction based on the first continuous coordinate and the second continuous coordinate; and obtaining the first dimensional coordinate and the second dimensional coordinate based on the vertical distance from the projected response line to the preset original point, and the included angle.

18. The non-transitory computer-readable storage medium of claim 17, wherein the computer program is further configured to, when executed by the processor, causes the processor to perform, based on the weighted value, a weighting processing on the response line generated based on the dimensional coordinates in the sinogram.

* * * * *